US006306349B1

United States Patent
Moon et al.

(10) Patent No.: US 6,306,349 B1
(45) Date of Patent: Oct. 23, 2001

(54) CATALYST CHARACTERIZATION APPARATUS

(75) Inventors: Dong Ju Moon; Kun You Park; Moon Jo Chung; Byoung Sung Ahn, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/449,467

(22) Filed: Nov. 29, 1999

Related U.S. Application Data

(63) Continuation of application No. 09/045,175, filed on Mar. 20, 1998, now abandoned.

(30) Foreign Application Priority Data

Mar. 21, 1997 (KR) .................................... 97/9808

(51) Int. Cl.[7] .................................... G01N 31/10
(52) U.S. Cl. .................. 422/69; 73/38; 422/78; 422/80; 436/5; 436/37; 436/159
(58) Field of Search ............... 422/68.1, 69, 78, 422/80; 436/37, 5, 159; 73/38, 869.5, 866

(56) References Cited

U.S. PATENT DOCUMENTS 4,489,593  12/1984  Pieters et al. .
5,342,580  8/1994  Brenner .

OTHER PUBLICATIONS

"A Multifunctional in situ Catalyst Characterization Apparatus" –*Applied Catalyist*, 19 (1985) 119–139 by Carlos Serrano and J.J. Carberry.
"Adsorption of Gases in Multimolecular Layer" –*J. Amer. Chem. Soc.*, 60 (1938) 309 by Stephen Brunauer et al.
"Deactivation of Pd Catalysts in the Hydrodechlorination of chloropentafluroethane" –*Applied Catalysis* A:General 168(1), 1998) 159–170 in press by Moon et al. (cover date Mar. 13, 1998.

*Primary Examiner*—Jan Ludlow
(74) *Attorney, Agent, or Firm*—Morrison & Foerster LLP

(57) ABSTRACT

The present invention relates to a catalyst characterization apparatus, and in particular to an improved catalyst characterization apparatus which is capable of characterizing the surface of a catalyst more accurately by a volumetric method without requiring a pre-treatment step which may vary the characteristics of the catalyst as well as without exposing the catalyst in air, by combining a dynamic flow type reactor with a volumetric type adsorption apparatus, whereby it is possible to accurately characterize the catalyst during an actual reaction. It is possible to accurately characterize the various catalysts and to characterize the catalyst during the reaction, alternately and/or continuously, by combining a dynamic flow type reactor with a volumetric type characterization apparatus as well as a dynamic flow type characterization apparatus.

6 Claims, 2 Drawing Sheets

CATALYST CHARACTERIZATION APPARATUS

This application is a continuation of Ser. No. 09/045,175 filed Mar. 20, 1998, now abandoned.

BACKGROUND OF THE INVENTION

1. Field of the Invention

The present invention relates to a catalyst characterization apparatus, and in particular to an improved catalyst characterization apparatus which is capable of more accurately characterizing surface properties of a catalyst by a volumetric method without exposing the catalyst in air, by combining a dynamic flow type chemical reactor with a volumetric type adsorption apparatus, performing a gaseous catalytic reaction, and characterizing the catalyst, alternately and/or continuously.

2. Description of the Conventional Art

In order to measure activity, selectivity, and deactivation of a heterogeneous catalyst, and understand a reaction mechanism thereof, it is necessary to characterize the catalytic properties such as an internal composition, a physical structure, and physical and chemical surface properties of a catalyst.

There are several methods for characterizing catalyst, such as a method of using an X-ray, a method of using an electron microscope, etc. A very important method for characterizing the catalyst uses an adsorption phenomenon on a catalyst surface. The method for characterizing catalyst using the adsorption phenomenon is classified into a volumetric type method and a dynamic flow type method.

The volumetric type catalyst characterization method is directed to measuring an adsorption balance of gas with respect to the catalyst surface and characterizing the catalyst, thus obtaining a relatively accurate characterization result. However, the measurement is time consuming, and the property of the catalyst may be varied during the preparation and pre-treatment process of a catalyst sample.

The dynamic flow type method for characterizing a catalyst is directed to a method of measuring the stage of non-equilibrium adsorption which varies dynamically, when gas flows through the catalytic layer. This method is simple compared to the volumetric type method, and the characterization time is shortened. However, since the measurement result is affected by the adsorption property of the catalyst and the operation condition, this method is less accurate compared with the volumetric type method.

The volumetric type adsorption apparatus which is used for the volumetric type method for characterizing a catalyst, as shown in FIG. 1, includes a manifold 1 connected to a standard volume tube 2, a sample tube 3, an adsorption gas and helium gas supply source 4, a vacuum pump 5, and through valves V1, V2, V3 and V4, respectively.

The standard volume tube 2 is a container used as a standard for measuring an internal volume. The container is filled with a liquid such as mercury, and then the internal volume is accurately measured before the container is attached to the apparatus. An absolute pressure gauge 6 is installed in the manifold 1.

The procedure of measuring an adsorption property of the catalyst using a volumetric adsorption apparatus will now be explained.

The standard volume tube valve V1 and the gas supply valve V3 are closed, and then the sample tube valve V2 and the vacuum pump valve V4 are opened. Thereafter, the vacuum pump 5 is operated by connecting the sample tube 3 to the vacuum pump 5 through the manifold 1, and then the sample tube 3 is ventilated. The sample tube valve V2 and the vacuum pump valve V4 are closed, and gas such as He which is regarded as an ideal gas from the adsorption gas and helium gas supply source 4 fills the standard volumetric tube 2 through the manifold 1. At this time, pressure P1 is measured by using an absolute pressure gauge 6. The standard volumetric tube valve V1 and the gas supply valve V3 are closed thereby to close the standard volumetric tube 2. The adsorption gas, an helium gas supply source 4 and then the vacuum pump valve V4 are opened, and the manifold 1 is ventilated by the vacuum pump 5. After the interior of the manifold 1 is vacuumized, the vacuum pump valve V4 is closed, and the standard volumetric tube valve V1 is opened, thus supplying gas from the standard volumetric tube 2 to the manifold 1. Afterwards a final equilibrium pressure P2 is measured by the absolute pressure gauge 6. The volume of the manifold 1 is obtained by using an interrelationship between the pressure and volume of the gas with respect to the pressures P1 and P2 based on Boyle's law. The standard volumetric tube valve V1 and the gas supply valve V3 are closed, the sample valve V2 and the vacuum pump valve V4 are opened, then the manifold 1 and the sample tube 3 are ventilated by the vacuum pump 5. The sample valve V2 and the vacuum pump valve V4 are closed, and the gas supply valve V3 is opened. Thereafter, gas such as helium from the gas supply source 4 fills the manifold 1, the gas supply valve V3 is closed, the pressure P3 is measured by the absolute pressure gauge 6, the sample tube valve V2 is opened, the gas from the manifold 1 is supplied to the sample tube 3, and the final equilibrium pressure P4 is measured. Thereafter, the volume (the volume excluding the catalyst) is obtained by using an interrelationship between the pressure and volume of the gas with respect to the pressures P3 and P4 based on Boyle's law.

Therefore, it is possible to measure the amount of gases adsorbed into the catalyst based on the equilibrium pressure differences between the equilibrium pressure when the gas was not adsorbed on the catalyst based on the pressure-volume interrelationship between the manifold 1 and the sample tube 3, and the equilibrium pressure when the gas is adsorbed on the sample.

In order to measure the surface area of the catalyst, the physical adsorption of nitrogen is performed, thus measuring a BET surface area, a volume of a pore, and a mean diameter of pores. In order to measure the surface area of a metal, the amount of chemical adsorption of hydrogen and CO which are selectively adsorbed into the metal surface is measured, and it is possible to measure the surface area of the metal of the catalyst surface and the mean size of metal particles.

In addition, as the catalyst characterization method using a dynamic flow type characterization apparatus, a gas pulse chemical adsorption method which is mainly used for measuring the surface area of a metal of a catalyst, and a temperature programmed desorption technique for studying an adsorption state of a gas adsorbed on the catalyst are generally used.

In the gas pulse chemical adsorption method, a supported metal catalyst is pre-treated in a reactor, and then the system is ventilated by using a vacuum pump. The adsorption gas is supplied to the reactor by a sample injection valve having a sample loop of a predetermined volume together with an inert carrier gas, which is then adsorbed into the catalytic layer. The pulse adsorption operation is repeated by the sample injection valve until the concentration of adsorption gas at the gas outlet of the reactor is constant, and the amount of chemically adsorbed gas is calculated based on the difference between the amount injected in a pulse form and the amount of gas measured at the outlet of the reactor.

The temperature programmed desorption (TPD) method which is one of the temperature programmed techniques is a non-equilibrium method, wherein a measured gas is adsorbed on a sample, and then the gas adsorbed thereon and/or desorbed therefrom is characterized by using a gas chromatograph or a mass spectrograph, with continuously increasing the temperature of the sample, thus studying the state of the chemical adsorption. As another technique among the temperature programmed techniques is a temperature programmed reduction (TPR) method which is directed to measuring the amount of hydrogen, which is consumed when continuously increasing the temperature using an inert gas containing hydrogen, with a thermal conductivity detector (TCD), a gas chromatometer, or a mass spectrograph, thus studying reduced catalyst. As still another method among the temperature programmed techniques, there is a temperature programmed surface reaction (TPSR) method which is directed to adsorbing a reactant on a catalyst surface and then studying the reaction mechanism based on the consumption rate of the reactant gas, or a production rate of the product when continuously increasing the temperature by using an inert gas containing another reactant gas.

In the conventional method, when characterizing catalyst by using a separate apparatus from the catalytic reactor, the catalytic property is often changed during the process of performing a required pre-treatment, i.e., after the catalyst used for a reaction is removed from the reactor and is moved to the apparatus for characterizing catalyst.

Therefore, in order to check the catalytic property during the reaction, the catalytic property must be characterized without removing the catalyst from the reactor, but in situ (in the reactor).

As a conventional apparatus for accomplishing this object, is a catalyst characterization apparatus combining a dynamic flow type reactor with a dynamic flow type characterization apparatus (hereinafter, referred to as a "dynamic flow type reaction dynamic flow type characterization apparatus"), and a catalyst characterization apparatus combining a batch type reactor with a volumetric type adsorption apparatus (hereinafter, referred to as a "batch type reaction volumetric flow type characterization apparatus").

The dynamic flow type reaction dynamic flow type characterization apparatus was proposed by Carberry et. al. (Appl. Catal., 19 (1985), 119–139), which is capable of characterizing a sample without exposing a sample in air. However, since the amount of chemical adsorption is varied in accordance with the adsorption property of a metal and the pulse period and flux of a gas, it is impossible to accurately measure the amount of chemical adsorption, thus lowering the reliability of the measurement.

The batch type reaction volumetric type characterization apparatus was proposed by Brunauer et. al. (J. Am. Chem. Soc. 60 (1938) 309), which is capable of obtaining comparatively accurate experimental data, but since almost all catalytic reaction is proceeded in the dynamic flow type reactor, it is difficult to apply the apparatus in the actual reaction.

SUMMARY OF THE INVENTION

Accordingly, it is an object of the present invention to provide a catalyst characterization apparatus which overcomes the aforementioned problems encountered in the conventional art.

It is another object of the present invention to provide an improved catalyst characterization apparatus which is capable of characterizing a catalyst in a volumetric type method in which a catalyst used in a dynamic flow type reaction apparatus is placed in a reaction apparatus by combining a dynamic flow type chemical reactor with a volumetric type adsorption apparatus, so that a pre-treatment step which is used for the conventional volumetric type method is not required. Thus, it is possible to reduce a catalyst characterization time without sintering particles of the catalyst due to the repeated pre-treatment steps. Further, because the catalyst is not exposed in air, it is also possible to accurately characterize the catalyst during an actual reaction according to the present invention.

It is another object of the present invention to provide an improved catalyst characterization apparatus which is capable of variously and accurately characterizing the various catalysts by using a dynamic flow type catalyst characterization apparatus during actual reaction.

It is also another object of the present invention to provide an improved catalyst characterization apparatus which is capable of accurately controlling a pulse period and an injection time which affect a catalyst characterization result by using a dynamic flow type catalyst characterization apparatus and a sample injection valve with an electrical actuator.

To achieve the above objects, there is provided the catalyst characterization apparatus which comprises a dynamic flow type chemical reactor including a reactor and a reaction/transfer gas supply source, a volumetric adsorption apparatus in which a standard volumetric tube, an adsorption gas supply source, a high vacuum pump and an absolute pressure gauge are connected to a manifold, respectively.

Additional advantages, objects and features of the invention will become more apparent from the description which follows.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The catalyst characterization apparatus according to the present invention will now be explained with reference to the accompanying drawings.

Figure 1:
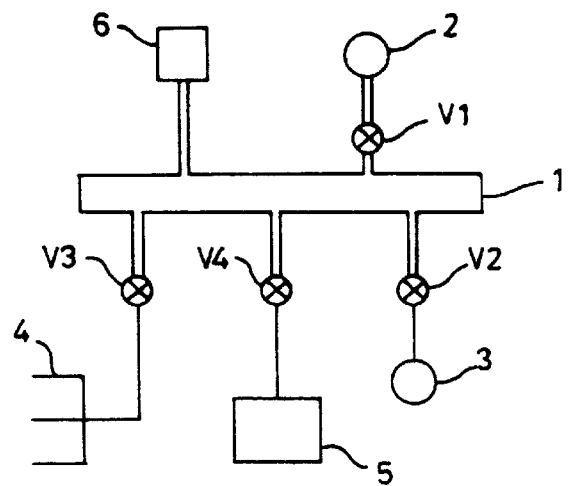
FIG. 1 is a schematic view illustrating a system of a conventional volumetric type adsorption apparatus.
Figure 2:
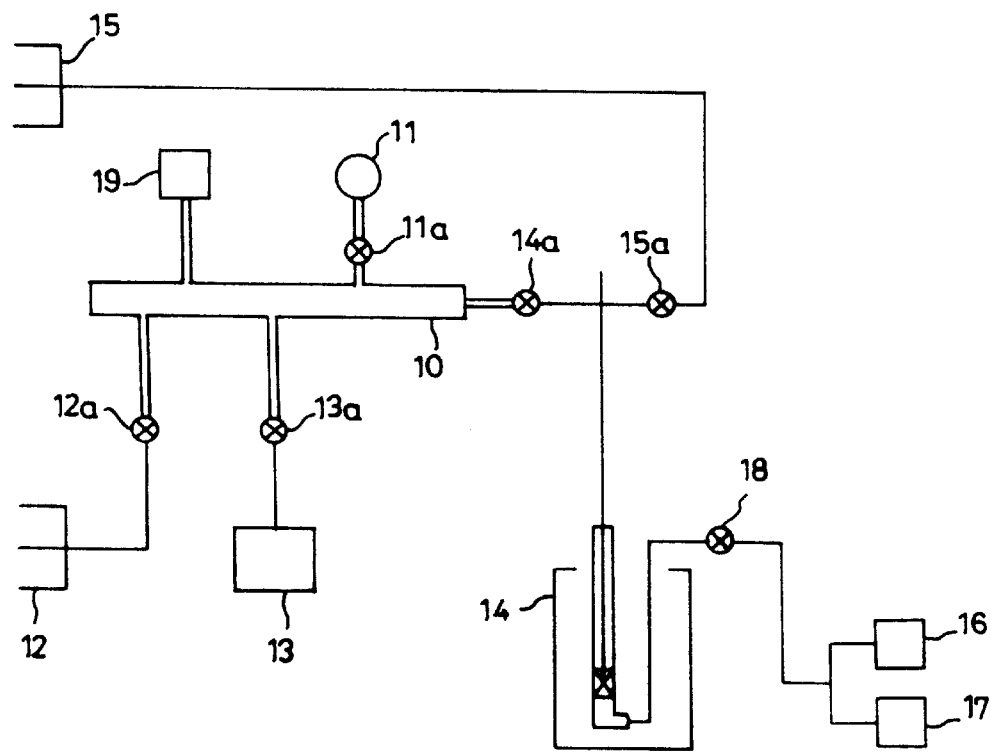
FIG. 2 is a schematic view illustrating a system of a dynamic flow reaction type/volumetric type catalyst characterization apparatus according to the present invention.

FIG. 2 illustrates a dynamic flow type reaction with volumetric catalyst apparatus according to the present invention. As shown therein, a standard volumetric tube 11, an adsorption gas supply source 12, and a high vacuum pump 13 are respectively connected to a manifold 10, which has an absolute pressure gauge 19, and through valves 11a, 12a and 13a. A reactor 14 is connected to the manifold 10 through a sample valve 14a, and a reaction/transfer gas supply source 15 are connected to the sample tube valve 14a through a reactant/transfer gas supply valve 15a. The gas discharged from an outlet of reactor 14 flows to the gas chromatograph 16, and a mass spectrometer 17 through a discharge valve 18.

As shown in FIG. 2, in order to characterize a catalyst using a dynamic flow type reaction type catalyst characterization apparatus according to the present invention, while a catalyst is charged into the reactor 14, and the reaction is performed, the reactant/transfer gas supply value 15a is closed, and the sample tube valve 14a and the vacuum pump valve 13a are opened. Thereafter, the vacuum pump 13a is operated in a state where the reactor 14 is connected to the vacuum pump 13 through the manifold 10, thus ventilating the reactor 14.

Next, the sample valve 14a and the vacuum pump valve 13a are closed, and the reactor 14 and the vacuum pump 13 are closed. Thereafter, the standard volumetric tube 11a and the adsorption gas supply valve 12a are opened. Gas such as He, etc. which are regarded as an ideal gas is filled from the adsorption gas supply source 12 into the standard volumetric tube 11. At this time, the pressure P1 therein is measured by an absolute pressure gauge 19, and the standard volume tube valve 11a and the adsorption gas supply valve 12a are closed, and the standard volume tube 11 and the adsorption gas supply source 12 are closed, and then the vacuum pump valve 13a is opened, and the manifold 10 is connected to the vacuum pump 13.

After the interior of the manifold 10 is fully evacuated, the vacuum pump valve 13a is closed, and the standard volume tube valve 11a is opened, and gas from the standard volume tube 11 is supplied to the manifold 10. Thereafter, the final equilibrium pressure P2 is measured by the absolute pressure gauge 19, and then the volume of the manifold 10 is obtained by an inter-relationship between the pressure and volume of the gas based on Boyle's law with respect to the pressures of P1 and P2.

The standard volume tube valve 11a and the gas supply valve 12a are closed, the test tube valve 14a and the vacuum pump valve 13a are opened, and the manifold 10 and the reactor 14 are connected to the vacuum pump 13. Thereafter, the sample tube valve 14a and the vacuum pump valve 13a are closed, and the gas supply valve 12a is opened. Gas such as He, etc. which are regarded as an ideal gas is filled from the gas supply source 12 into the manifold 10. The gas supply valve 12a is closed, the pressure P3 is measured by the absolute pressure gauge 19, the sample tube valve 14a is opened, so as to supply gas from the manifold 10 to the reactor 14. Thereafter, the final equilibrium pressure P4 is measured, and the volume (except the volume of the catalyst) of the reactor 14 is obtained by using an inter-relationship between the pressure and volume of the gas based on Boyle's law with respect to the pressures of P3 and P4.

The amount of gases adsorbed on the catalyst is measured based on the equilibrium pressure difference between the equilibrium pressure when the gas which is not adsorbed on the catalyst in accordance with a pressure-volume inter-relationship between the manifold 10 and the reactor 14 is used and the pressure when the gas which is adsorbed on the catalyst is used.

A BET surface, a pore volume and a mean pore diameter are measured by a physical adsorption of nitrogen, and the chemical adsorption amount of hydrogen and CO which are selectively adsorbed into the surface of a metal are measured; and, the number of metal atoms of the catalyst surface, the surface area of the metal, and the mean size of a metal particle are measured.

Hydrogenation reaction of a chloropentafluoroethan ($CF_3CF_2Cl$) (hereinafter, referred to as "CFC-115") over $Pd/\gamma-Al_2O_3$ catalyst is studied. The dispersion of Pd denotes a ratio of the number of atoms exposed to the surface with respect to the number of Pd atoms, and the size of a particle of Pd are measured based on a spherical particle.

Therefore, it is possible to characterize the property based on the measured value and the calculated value.

Figure 3:
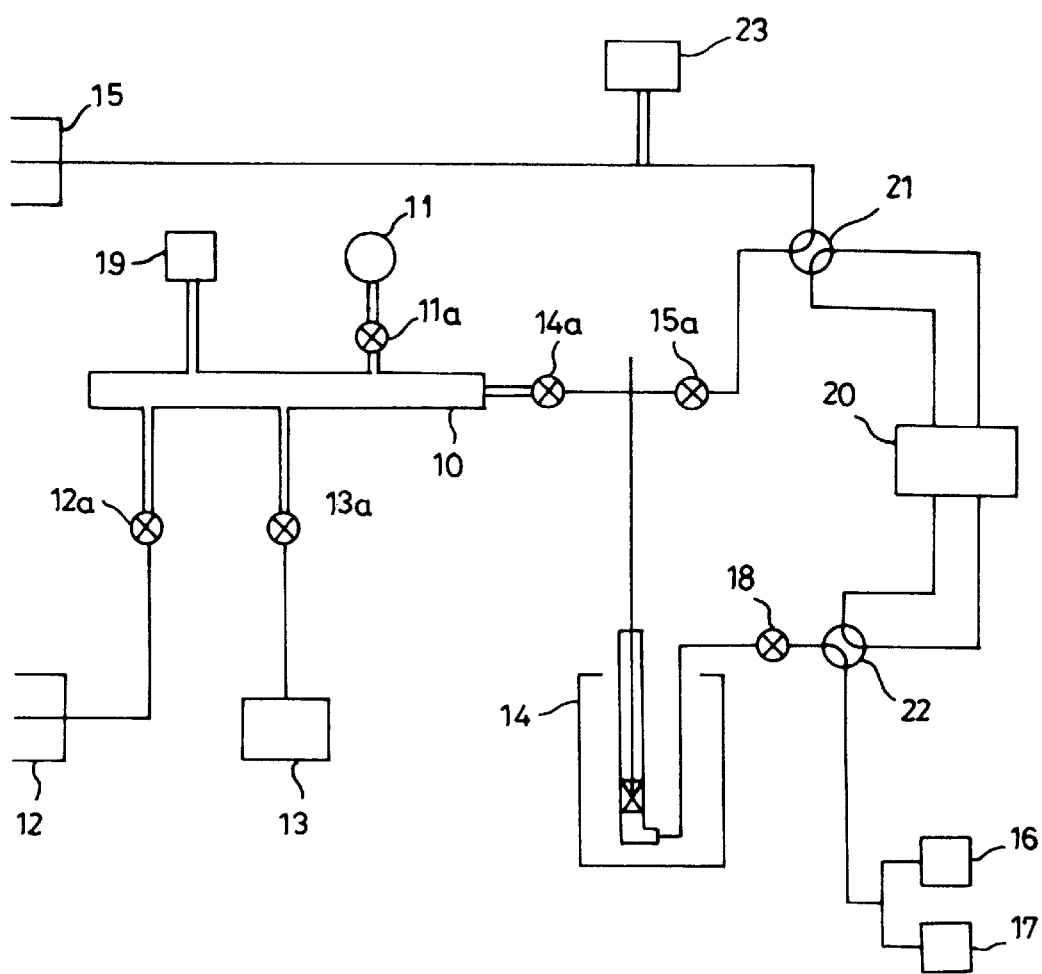
FIG. 3 is a schematic view illustrating a system of a dynamic flow reaction type/volumetric type, and dynamic flow type catalyst characterization apparatus according to the present invention.

FIG. 3 illustrates a dynamic flow type reaction volumetric type and dynamic flow type catalyst characterization apparatus which is configured by using the apparatus as shown in FIG. 2, and the dynamic flow type characterization apparatus according to another example of the present invention. As shown therein, 4-way valves 21 and 22 are installed between the reactant/transfer gas supply source 15 and a reactant/transfer gas supply valve 15a, and the reactor 14 and characterization apparatuses 16 and 17, and a thermal conductivity detector 20 is connected, and the sample injection valve 23 is installed at an intermediate portion of the reactant/transfer gas supply source 15.

The dynamic flow type reaction volumetric type catalyst characterization apparatus according to the present invention will now be explained with reference to FIG. 3.

First, a catalyst is charged into a reactor. The adsorption gas supply valve 12a and the reactant/transfer gas supply valve 15a are closed, and then the standard volumetric tube valve 11a, the sample tube valve 14a, and the vacuum pump valve 13a are opened. The reactor 14 is connected to the vacuum pump 13 through the manifold 10, the vacuum pump 13 is driven, and the standard volumetric tube 11, the manifold 10, and the reactor 14 are evacuated.

The sample valve 14a and the vacuum pump valve 13a are closed, the reactor 14 and the vacuum pump 13 are closed, and the adsorption gas supply valve 12a is opened, so that a gas such as He, etc. is filled from the adsorption gas supply source 12 into the standard volume tube 11 through the manifold 10, and then the adsorption gas supply valve 12a is closed. Thereafter, the pressure P1 is measured by the absolute pressure gauge 19, the standard volume tube valve 11a is closed, and the vacuum pump valve 13a is opened, so that the manifold 10 is evacuated by the vacuum pump 13. After the interior of the manifold 10 is vacuumized, the vacuum pump valve 13a is closed, and the standard volume tube valve 11 is opened, so that the gas in the standard volume tube 11 is supplied to the manifold 10. The final equilibrium pressure P2 is measured by the absolute pressure gauge 19, and the volume of the manifold 10 is computed by using an interrelationship between the pressure and volume of the gas based on Boyle's law with respect to the pressures of P1 and P2.

Again, the standard volume tube valve 11a is closed, the sample tube value 14a is opened, and the gas is supplied from the manifold 10 into the vacuum reactor 14. The final equilibrium pressure P3 is measured by the absolute pressure gauge 19, and then the volume of the reactor 14 except the actual volume of the catalyst is obtained based on Boyle's law with respect to the pressures of P2 and P3.

The volume of the gas adsorbed into the catalyst is measured based on an equilibrium pressure difference between a equilibrium pressure when the gas is not adsorbed on the sample based on a pressure-volume inter-relationship between the manifold 10, the reactor 14 and a equilibrium pressure when the gas is adsorbed into the sample.

The catalyst is characterized during a reaction as follows.

A predetermined amount of the catalyst is provided in the reactor 14, and then the catalyst is reduced under hydrogen flowing. Thereafter, the hydrogen reaction is performed under the reaction condition by providing a reactants. At this time, the hydrogen chloride and hydrogen fluoride produced during the reaction are removed by passing the same through a solution of 0.1M sodium hydroxide, and moisture is removed by passing the same through a drying tube (not shown) into which calcium chloride is filled. The reaction product is characterized by using the gas chromatograph 16 and the mass spectrometer 17. When the characterization of the catalyst is needed, the reactor system purged by helium gas at a reaction temperature after the reaction is terminated.

At this time, the reactant/transfer gas supply valve 15a and the discharge valve 18 are closed, the sample valve 14a is opened, and the interior of the reactor is ventilated at a reaction temperature, so that the volume of the gas adsorbed into the catalyst is measured in the same method as the catalyst characterization method.

After characterizing the catalyst, the reaction system is set at a reaction temperature, and then the sample valve 14a is closed, and the reactant/transfer gas supply valve 15a and the discharge valve 18 are opened. Thereafter, the reactor 14 is purged by He, and the reaction is continued by providing a reaction gas, or the reaction and characterization may be alternately performed in the same manner.

In the above-described manner, the reaction which is being performed is stopped. Argon gas is ventilated from the reactor 14, and then the reactant/transferring gas supply valve 15a and the discharge valve 18 are closed, and the test tube valve 14a is opened for thus ventilating the reactor 14 at a reaction temperature. Thereafter, the test tube valve 14a is closed, and then the reactor is closed. Thereafter, the reactant/transfer gas supply valve 15a and the discharge valve 18 are opened.

The 4-way valve 21 and the 4-way valve 22 are turned clockwise, thus allowing the flow of carrier gas through the thermal conductivity detector 20. When the thermal conductivity detector 20 is turned on, and the system is stabilized, hydrogen gas is provided into a transfer gas by using the sample injecting valve 23 to which an electric actuator is fixed.

The transfer gas containing a predetermined amount of hydrogen flows through the 4-way valve 21 and then is transferred to the reactor 14 through a reference side of the thermal conductivity detector 20. Some of adsorption gas is adsorbed on the surface of the catalyst, and the gas not adsorbed flows to the sample side of the thermal conductivity detector 20 through the 4-way valve 22 together with He transfer gas.

The surface of sample is saturated by the adsorption gas, and the adsorption gas is periodically injected 5 to 10 times through the sample injectionl valve 23 until the concentration of adsorption gas of the outlet is constant.

The amount of gases which are chemically adsorbed is computed based on the difference between the amount of the gases introduced into the reactor 14 and the amount of the gases discharged from the same. The transfer gas of the system may be changed by the reactant/transfer gas supply source 15 in accordance with the kind of the adsorption gas.

The catalyst characterization apparatus according to the present invention may be easily used as the conventional volumetric and dynamic flow type characterization apparatus by switching the valves during the dynamic flow type chemical reaction. The catalyst property in the real reaction condition is characterized at any time when the characterization of the catalyst is needed during the reaction. Even after the characterization, the reaction may be continued again. Various catalyst characterization techniques such as BET surface area measuring, pore size measuring, chemical adsorption, gas pulse chemical adsorption, temperature programmed desorption, temperature programmed reduction, temperature programmed surface reaction, reaction and deactivation mechanism study, metal particle growing rate study, reaction and adsorption kinetic study, pulse experiment of an isotope, etc. may be applied by the catalyst characterization apparatus.

EXAMPLES

Example 1

As shown in FIG. 2, the dynamic flow type reaction volumetric type catalyst characterization apparatus was designed and constructed. A standard volumetric tube 11 with a volume of 25.525 cc was connected to a separating tube 10 by welding a stainless tube having an outer diameter of 12.5 mm. A high vacuum pump 13, a turbo molecular pump which is capable of ventilating up to $1.0 \times 10^{-9}$ torr was used.

A U-shaped reactor 14 which is formed of a quartz tube having a length of 25 cm and an inner diameter of 7 mm was controlled at a temperature within a range of $\pm 1°$ C. by using an electric furnace (not shown) with a temperature controller and was heated up to 800° C. at a rate of 30° C./minute.

An absolute pressure gauge 19 with a resolving power of $1 \times 10^{-3}$ torr with respect to a pressure variation, and valves 11a, 12a, 13a, 14a, 15a, and 18 were all designed to endure a high vacuum pressure. The gas chromatograph 16 and mass spectrometer 17 which are characterization apparatuses were connected on-line with the 4-way valve 22. In order to correct a measuring error due to the temperature, all apparatuses except for the above-described characterization apparatuses were installed in the constant temperature system as shown in FIG. 2.

Example 2

The dynamic flow type reaction volumetric type and dynamic flow type catalyst characterization apparatuses according to the present invention as shown in FIG. 3 were designed and constructed.

A sample injection valve 23 which is driven by an electric actuator was installed in the dynamic flow type reaction volumetric type catalyst characterization apparatus which was designed in the same manner as Example 1 and according to the present invention, and the thermal conductivity detector 20 was connected by two 4-way valves 21 and 22.

The sample injection valve 23 includes a six-port valve with an electric actuator (not shown), and a sampling loop with a volume of 0.1 cc was attached thereto for supplying an adsorption gas sample.

The sample injection valve 23 was adjusted to correctly control the interval of sample injection and injection time, which influences the characterization results, by using a time controller (not shown).

The thermal conductivity detector 20 was used for a characterization operation in a dynamic flow type characterization method. A filament may be made of various materials in accordance with the property of gas to be characterized. In the present invention, a nickel filament having a durability with respect to hydrochloric acid and hydrofluoric acid was used.

Example 3

The 4% Pd/y-Al$_2$O$_3$ catalyst of 0.1 g was charged in a reactor 14 of the catalyst characterization apparatus according to Example 2 of the present invention. The high vacuum pump 13 was evacuated at a temperature of 300° C. for three hours, thus forming a pressure of 2×10$^{-4}$ torr therein. The sample unit of the reactor 14 was immersed into a liquid nitrogen dewer, and the BET surface area was measured by using nitrogen adsorption. As a result of the measurement, the BET surface area of the catalyst was 180.7 m$^2$/g.

Example 4

The 4% Pd/y-Al$_2$O$_3$ catalyst of 0.1 g was charged in a reactor 14 of the catalyst characterization apparatus according to Example 2 of the present invention, and then the catalyst was reduced under hydrogen flowing at a temperature of 300° C. for three hours. Thereafter, the reactor 14 was ventilated to a pressure of 2×10$^{-5}$ torr for two hours at the same temperature. The temperature in the reactor 14 remained at room temperature. The internal volume of the reactor except for the catalyst was measured by using Helium gas. A first adsorption isotherm line was obtained through an adsorption experiment performed with respect to Hydrogen by increasing the pressure of Hydrogen. In order to remove the reversibly adsorbed hydrogen and the hydrogen absorbed into palladium, the reactor 14 was evacuated to 2×10$^{-5}$ torr for 20 minutes, and thereafter, the hydrogen adsorption experiment was performed, thus obtaining a second adsorption isotherm. The Pd surface area, the Pd dispersion and the size of particles were 4.61 m$^2$/g, 0.334 and 3.38 nm, respectively, based on the difference between two adsorption equivalent lines.

Example 5

As shown in FIG. 3, the 4% Pd/y-Al$_2$O$_3$ catalyst of 0.1 g was charged in a reactor of the catalyst characterization apparatus according to the present invention, and the catalyst was reduced under hydrogen flowing for 3 hours at a temperature of 300° C. Thereafter, hydrogen was provided thereinto at 6 cc/min, and CFC-115 was provided thereinto at 3 cc/min. The hydrogenation reaction was performed for 24 hours at a reaction temperature of 260° C. Thereafter, the reaction was evacuated. The reactor was ventilated to a pressure of 2×10$^{-5}$ torr for two hours at a temperature of 300° C. The hydrogen adsorption experiment was performed under the same condition as Example 2. As a result of the experiment, the Pd surface area, the Pd dispersion and the size of particle were 1.89 m$^2$/g, 0.107 and 10.46 nm, respectively.

Comparative Example 1

A BET surface area was measured in the same method as Example 3 by using a volumetric type adsorption apparatus made of glass with a standard volumetric tube of 23.05 cc and a manifold of 51.50 cc. As a result of the measurement, the surface area of the Pd/y-al203 catalyst was 181.6 m$^2$/g. Within the experiment error range, this result was identical to the result of Example 3 which was performed by using the apparatus according to the present invention.

Comparative Example 2

A hydrogen adsorption experiment was performed under the same condition as Example 4 by using the apparatus according to the comparative Example 1 according to the present invention. As a result of the experiment, the Pd surface area, the Pd dispersion and the size of particles of the Pd/y-Al203 were 4.55 m$^2$/g, 0.258 and 4.35 nm, respectively. Within the experiment error range, this result was identical to the result of Example 4 which was performed by using the apparatus according to the present invention.

Comparative Example 3

A hydrogen adsorption experiment was carried out under the same condition as Example 4 by using the dynamic flow type characterization apparatus according to the present invention. As a result of the hydrogen pulse adsorption experiment which was performed at a temperature of 25° C., the Pd surface area, the Pd dispersion and the size of particles of the Pd/y-Al203 catalyst were 3.95 m$^2$/g, 0.224 and 5.0 nm, respectively. When comparing the results of measurement which was performed by using the apparatus and volumetric type apparatus according to the present invention, an error which exceeds an experiment error range occurred. Therefore, the result which was obtained by using the dynamic flow type characterization apparatus is inaccurate compared to the result of the volumetric type characterization apparatus.

Comparative Example 4

A hydrogenation reaction was performed under the same condition as Example 5. Thereafter, the reaction was stopped, and the reactor was evacuated by Helium gas. The catalyst was withdrawn from the reactor, and then the catalyst was reduced by the same method as Example 4, and the reactor was evacuated. The hydrogen adsorption experiment was performed by the same method as Example 5. As a result of the experiment, the Pd surface area, the Pd dispersion, and the size of particles of the Pd/yAl203 catalyst were 1.52 m$^2$/g, 0.086 and 13.01, respectively.

Result of the characterization of catalysts which were obtained in the above-described Examples and Comparative Examples according to the present invention are shown in Table 1. Example 3 and Comparative Example 1 were directed to measuring the surface area of the Pd/y-Al203 catalyst by using the apparatus according to the present invention and the volumetric type adsorption apparatus.

Since the BET surface area measured in accordance with the present invention and the result measured by the volumetric adsorption apparatus were within the experimental result, it was found that the result obtained by using the apparatus according to the present invention is reliable.

In Examples 4 and 5, the Pd surface area of the Pd/y-Al203 catalyst before the reaction was measured, the result measured by the apparatus according to the present invention and the result measured by the volumetric adsorption apparatus were coincided; however, there was a difference between the result measured by the dynamic flow type characterization apparatus and the result measured by the volumetric adsorption apparatus. Therefore, it was determined that the result which was obtained by the dynamic flow type characterization method was more unreliable compared to the result obtained by the volumetric method.

In Examples 4 and 5, the resultant values were obtained, which were obtained by stopping the reaction after the hydrogenation reaction of CFC-115 was performed for 24 hours based on the Pd/y-Al203 catalyst and then performing a chemical adsorption experiment of hydrogen. As a result, the difference between the result obtained by the apparatus according to the present invention and the result obtained by the volumetric adsorption apparatus exceeds the measuring error range. The above-described difference was obtained because the property of the catalyst exposed in air for characterizing the catalyst using the volumetric adsorption apparatus was changed. If the catalyst was exposed in air, the metal state Pd was oxidized, and becomes PdO. If the resultant material was deoxidized at a high temperature, it becomes PdH, and if the resultant material was evacuated, it becomes Pd particle. Therefore, the dispersed metallic particles were grown, and the property of the catalyst was changed.

In the catalyst characterization apparatus according to the present invention, the catalyst was not exposed in air. Namely, the property of the catalyst was characterized based on the volumetric adsorption method in which a pre-treating was not performed which may change the property of the catalyst, so that it is possible to accurately measure the property of the catalyst under an actual reaction condition.

is applied to an actual characterization of a catalyst (Appl. Catal. A. 168(1), 1998, 159–170) as follows: "The deactivation behavior of Pd catalysts on different supports in the hydrodechlorination of chloropentafluoroethane ($CF_3CF_2Cl$) was investigated. Changes of the BET surface area and the metal percentage exposed, measured by a multipurpose in situ catalyst characterization apparatus during the reaction gave some information about the deactivation mechanism of the Pd catalysts. The deactivation of the Pd catalysts was mainly caused by sintering of Pd particles rather than by coking. The sintering of Pd particles on the catalyst surface was promoted by the reaction of hydrogen fluoride with the support of the catalyst."

Although the preferred examples of the present invention have been disclosed for illustrative purposes, those skilled in the art will appreciate that various modifications, additions and substitutions are possible, without departing from the scope and spirit of the invention as recited in the accompanying claims.

TABLE 1

| | Method used | BET surface area ($m^2$/g-catalyst) | Pd surface area (m2/g-catalyst) | Dispersion (D) | size of particle (nm) |
|---|---|---|---|---|---|
| Example 3 | Dynamic flow type reaction volumetric adsorption apparatus | 180.7 | — | — | — |
| Example 4 | Dynamic flow type reaction volumetric adsorption apparatus | — | 4.61 | 0.334 | 3.38 |
| Example 5 | Dynamic flow type reaction volumetric adsorption apparatus | — | 1.89 | 0.107 | 10.46 |
| Comparative Example 1 | Volumetric adsorption apparatus | 181.6 | — | — | — |
| Comparative Example 2 | Volumetric adsorption apparatus | — | 4.55 | 0.258 | 4.35 |
| Comparative Example 3 | Dynamic flow type reaction Dynamic flow type characterization apparatus | — | 3.95 | 0.224 | 5.00 |
| Comparative Example 4 | Volumetric adsorption apparatus | — | 1.52 | 0.086 | 13.01 |

As described above, in the present invention, it is not necessary to remove the catalyst, which is used in the dynamic flow type reaction apparatus, to the characterization of catalyst. By combining the volumetric adsorption apparatus and the dynamic flow type reaction apparatus or the dynamic flow type reaction volumetric apparatus and the dynamic flow type characterization apparatus, so that it is possible to characterize the catalyst in the reaction apparatus without exposing the catalyst in the air, thus obtaining an accurate result of the characterization operation by the volumetric method. In addition, in the present invention, the pre-treatment operation which is used in the conventional art is not needed, thus significantly reducing the characterization time. Furthermore, the particles of the catalyst were not grown since the pre-treatment operation is not performed, so that the property of the catalyst is accurately characterized in the reaction condition. By combining the apparatus according to the present invention and the dynamic flow type catalyst characterization apparatus, it is possible to characterize the various catalysts during an actual reaction. It is possible to avoid any effects by the operation condition by combining the apparatus according to the present invention with the dynamic flow type catalyst characterization apparatus, a sample injection valve with an electric actuator, and accurately controlling the pulse period and injection time which influence the characterization result.

Furthermore, the catalyst characterization apparatus according to the present invention proposed by Moon et al.

What is claimed is:

1. A catalyst characterization apparatus, comprising:
   a dynamic flow chemical reactor comprising a reactor and a reactant/transfer gas supply source for supplying a reactant/transfer gas;
   a volumetric adsorption apparatus comprising a manifold, a standard volumetric tube, an adsorption gas supply source for supplying an adsorption gas, a high vacuum pump and an absolute pressure gauge; and
   control means for alternatively flowing the reactant/transfer gas and the adsorption gas through the reactor, wherein:
   said reactor, said reactant/transfer gas supply source, said standard volumetric tube, said adsorption gas supply source, said high vacuum pump and said absolute pressure gauge are connected to said manifold and
   said control means is located on a tee between said reactor, said reactant/transfer gas supply source and said manifold.

2. The apparatus of claim 1, wherein said standard volumetric tube, adsorption gas supply source, and high vacuum pump are connected to said manifold via corresponding valves, respectively, said reactor is connected to said manifold via a sample valve, said reactant/transfer gas supply source is connected to said manifold via a reactant/transfer gas supply source valve, said reactant/transfer supply source valve is connected to said sample valve, and a gas chromatograph and a mass spectrometer are connected to said reactor via a discharge valve.

3. The apparatus of claim 1, wherein a dynamic flow characterization apparatus is installed between the reactor and the reactant/transfer gas supply source.

4. The apparatus of claim 3, wherein said dynamic characterization apparatus comprises a thermal conductivity detector and is connected at one end between said reactant/transfer supply source and said reactant/transfer supply source valve via a four-way valve, and the other end of said thermal conductivity detector is connected between said discharge valve and said gas chromatograph and mass spectrometer via another four-way valve.

5. The apparatus of claim 1, further comprising a thermal conductivity detector connected at one end between said reactant/transfer gas supply source and said manifold via a four-way valve, and the other end of said thermal conductivity detector is connected between said reactor and a gas chromatograph via another four-way valve.

6. The apparatus of claim 5, wherein said standard volumetric tube, adsorption gas supply source, and high vacuum pump are connected to the manifold via corresponding valves, respectively, said reactor is connected to said manifold via a sample valve, said reactant/transfer gas supply source is connected to said manifold via said reactant/transfer gas supply source valve, said reactant/transfer supply source valve is connected to said sample valve, and said gas chromatograph and a mass spectrometer are connected to said reactor via said discharge valve.

* * * * *